US00PP08568P

United States Patent [19]

Warriner, deceased

[11] Patent Number: Plant 8,568

[45] Date of Patent: Feb. 1, 1994

[54] GRANDIFLORA ROSE PLANT NAMED 'JACANGEL'

[75] Inventor: William A. Warriner, deceased, late of Tustin, Calif., by Alene B. Warriner, legal representative

[73] Assignee: Bear Creek Gardens, Inc., Medford, Oreg.

[21] Appl. No.: 883,101

[22] Filed: May 14, 1992

[51] Int. Cl.[5] ..... A01H 5/00

[52] U.S. Cl. ..... Plt./11

[58] Field of Search ..... Plt. 11, 12, 13, 22

*Primary Examiner*—Howard J. Locker

*Attorney, Agent, or Firm*—Klarquist, Sparkman, Campbell, Leigh and Whinston

[57] ABSTRACT

A grandiflora rose high centered flowers of two-tone lavender purple color. It is resistant to powdery mildew and rust.

1 Drawing Sheet

The present invention relates to a new and distinct variety of rose plant of the Grandiflora class which was originated by me by crossing an unnamed seedling, with the variety Angel Face, U.S. Plant Pat. No. 2,792.

The primary objective of this breeding was to produce a new rose variety having the vigor and flower color of Angel Face combined with the high centered flower form of the unnamed seedling female parent. The objective was substantially achieved along with other desirable improvements as evidenced by the following unique combination of characteristics which are outstanding in the new variety and which distinguish it from its parents, as well as from all other varieties of which I am aware:

1. Unusal two-tone lavender purple color;
2. Resistance to powdery mildew and rust;
3. Excellent high centered flower form.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—An unnamed seedling.

*Pollen parent.*—Angel Face, U.S. Plant Pat. No. 2,792.

Classification:

*Botanical.*—*Rosa hybrida.*

*Commercial.*—Grandiflora.

FLOWER

Observations made from specimens grown in a garden environment in Somis, Calif. from July–October of 1991.

Blooming habit: Recurrent.

Bud:

*Size.*—1½" when the petals start to unfurl.

*Form.*—The bud form is: Short, pointed ovoid.

*Color.*—When sepals first divide, bud color is Red Purple Group 60A. When half blown, the upper sides of the petals are Red Purple Group 60A on the petal fringes becoming Red Purple 65B in the flower center; and the lower sides of the petals are Red Purple 60A.

*Sepals.*—Color: Green Group 138A. Surface texture: Covered with fine hairs. There are three normal to heavily appendaged sepals. There are two unappendaged sepals with hairy edges.

*Receptacle.*—Color: Green Group 138B. Shape: Funnel. Size: Small, ⅜"×¼". Surface: Glandular.

*Peduncle.*—Length: Medium, 2½" long. Surface: Glandular. Color: Medium green. Strength: Stiff, erect.

Bloom:

*Size.*—Medium. Average open size is 4".

*Borne.*—Singly.

*Stems.*—Medium, 12–14" strong.

*Form.*—When first open: High centered Permanence: Retains its form to the end, outer petals curl back.

*Petalage.*—Number of petals under normal conditions: 25–30.

*Color.*—The upper side of the petals is Red Purple Group 60A changing to Red Purple Group 65B in the center of the flower. The reverse side of the petals is Red Purple Group 60A. The base of the petals has a small yellowish white half moon at the point of attachment (¼"×¼"). The major color on the upper side is Red Purple Group 60A.

*Variegations.*—Occasional White streaks on the guard petals.

*Discoloration.*—The general tonality at the end of the first day: No change. At the end of the third day, General lightening of color to Red Purple Group 65B in the center of the flower. This color darkens again in day 5 or 6 back to Red Purple Group 60A due to sunlight.

*Fragrance.*—Moderate, lemon scent.

Petals:

*Texture.*—Thick.

*Shape.*—Round.

*Form.*—Tips slightly recurved, edges slightly quilled.

*Arrangement.*—Imbricated with few, small petaloids in the center.

*Persistence.*—Hang on and dry.

*Lastingness.*—On the plant: Long 7 days. As a cut flower: Long 7–9 days.

Reproductive parts:

*Anthers.*—Size: Medium. Quantity: Many. Color: Yellow. Arrangement: Regular around styles mixed with petaloids.

*Filaments.*—Color: White.

*Pollen.*—Color: Lemon yellow.

*Styles.*—Color: Yellowish white.

*Stigmas.*—Color: Greenish white.

Form: Bush.

Growth: Vigorous; medium; upright; branching.

Foliage:

*Number of leaflets on normal mid-stem leaves.*—5.

*Size.*—Medium $4\frac{1}{2}'' \times 3\frac{1}{2}''$.

*Quantity.*—Abundant.

*Color.*—New foliage: Reddish. Old foliage: Dark green, glossy.

Leaflets:

*Shape.*—Broadly oval.

*Texture.*—Upper side: Leathery, glossy.

*Edge.*—Serrated.

*Serration.*—Single, small.

*Petiole rachis.*—Color: Green.

*Petiole underside.*—Smooth, with prickles.

*Stipules.*—Medium, serrated.

*Disease resistance.*—Resistant to mildew and rust under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Medium, hooked downward.

*Color when young.*—Red.

Small prickles:

*Quantity.*—On main stalks: Many. On laterals: Many.

It is claimed:

1. A new and distinct variety of rose plant of the grandiflora class, substantially as herein shown and described, characterized particularly as to novelty by the unique combination of its novel two-tone lavender purple color, its excellent high centered flower form and its resistance to both powdery mildew and rust.

* * * * *

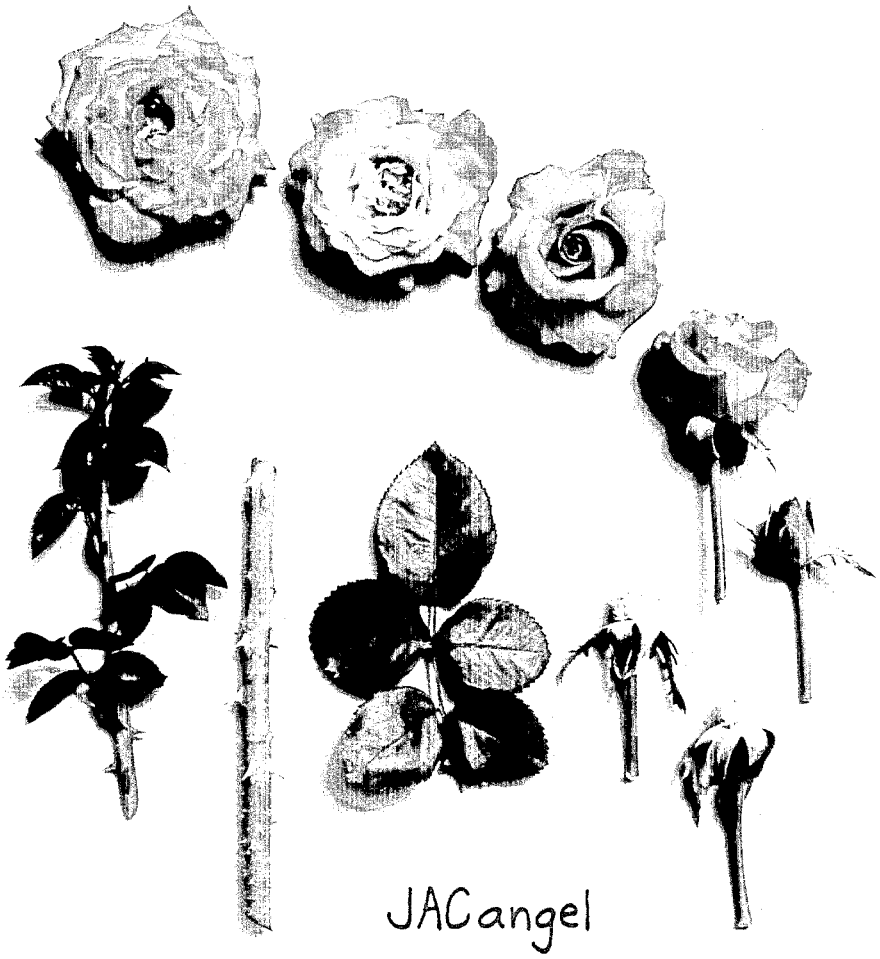
JACangel